US010168297B2

(12) United States Patent
Johnson, Jr. et al.

(10) Patent No.: US 10,168,297 B2
(45) Date of Patent: Jan. 1, 2019

(54) DNA-DECORATED GRAPHENE CHEMICAL SENSORS

(71) Applicant: The Trustees of The University of Pennsylvania, Philadelphia, PA (US)

(72) Inventors: Alan T. Johnson, Jr., Philadelphia, PA (US); Ye Lu, Philadelphia, PA (US); Brett R. Goldsmith, Philadelphia, PA (US); Nicholas J. Kybert, Haverford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/827,691

(22) Filed: Aug. 17, 2015

(65) Prior Publication Data

US 2015/0346141 A1    Dec. 3, 2015

Related U.S. Application Data

(62) Division of application No. 13/637,665, filed as application No. PCT/US2011/030484 on Mar. 30, 2011, now Pat. No. 9,146,209.

(60) Provisional application No. 61/319,062, filed on Mar. 30, 2010.

(51) Int. Cl.
*G01N 27/414* (2006.01)
*G01N 33/53* (2006.01)
*G01N 27/327* (2006.01)

(52) U.S. Cl.
CPC ..... *G01N 27/4145* (2013.01); *G01N 27/3278* (2013.01); *G01N 27/414* (2013.01); *G01N 33/5308* (2013.01)

(58) Field of Classification Search
None
See application file for complete search history.

(56) References Cited

U.S. PATENT DOCUMENTS

| | | |
|---|---|---|
| 6,326,215 B1 | 12/2001 | Keen |
| 2007/0132043 A1 | 6/2007 | Bradley et al. |
| 2009/0054272 A1 | 2/2009 | Prud'homme et al. |
| 2009/0084678 A1* | 4/2009 | Joshi .................. A61B 5/14532 204/403.14 |
| 2009/0321721 A1 | 12/2009 | Malenfant et al. |
| 2010/0025660 A1 | 2/2010 | Jain et al. |
| 2010/0140219 A1 | 6/2010 | Liang |
| 2010/0279426 A1* | 11/2010 | Tour ..................... B82Y 10/00 436/149 |
| 2010/0327847 A1* | 12/2010 | Leiber ................... B82Y 15/00 324/71.1 |

OTHER PUBLICATIONS

Ao, et al., "Enhancement of CO Detection in Al Doped Grapheme", Chemical Physics Letters 2008, 461(4-6), 276-279.
(Continued)

*Primary Examiner* — Betty J Forman

(74) *Attorney, Agent, or Firm* — Baker & Hostetler LLP

(57) ABSTRACT

The present invention provides a broad response single-stranded DNA-graphene chemical sensor device. The present invention also provides methods for improving the ability of graphene to work as a chemical sensor by using single-stranded DNA as a sensitizing agent.

16 Claims, 2 Drawing Sheets

Specification includes a Sequence Listing.

(56) References Cited

OTHER PUBLICATIONS

Chen, et al., "Intrinsic and Extrinsic Performance Limits of Graphene Devices on SiO2", Nature Nanotechnology, 2008, 3(4), 206-209.

Chen, et al., "Graphene Nano-Ribbon Electronics", Physica E-Low-Dimensional Systems & Nanostructures 2007, 40(2), 228-232.

Dan, et al., "Intrinsic Response of Graphene Vapor Sensors", Nano Letters 2009, 9(4), 1472-1475.

Ishigami, et al., "Atomic Structure of Graphene on Si02", Nano Letters, epub May 11, 2007, 7, 1643-1648.

Johnson, et al., "Free Energy Landscape of a DNA-Carbon Nanotube Hybrid Using Replica Exchange Molecular Dynamics", Nano Letters 2009, 9(2), 537-541.

Johnson, et al., "Probing the Structure of DNA-Carbon Nanotube Hybrids with Molecular Dynamics", Nano Letters, 2008, 8(1), 69-75.

Mohanty, et al "Graphene-Based Single-Bacterium Resolution Biodevice and DNA Transistor: Interfacting Graphene Derivatives with Nanoscale and Microscale Biocomponents", Nano Letters 2008, 8, 4469-4476.

Mohanty, et al, On Lie Supporting Document: "Graphene Based Single-Bacteriumm Biodevice and DNA Transistor: Interfacing graphene Derivatives with Nano and Micro Scale Biocomponents", Nano Letters, 2008, 8, 1-18.

Novak, et al., "Nerve Agent Detection Using Networks of Single-Walled Carbon Nanotubes", Applied Physics Letters, 2003, 83(19), 4026-4028.

Radosavljevic, et al "Novolatile Molecular Memory Elements Based on Ambipolar Nanotube Field Effect Transistors", Nano Letters, 2002, 761-764.

Robinson, et al., "Reduced Graphene Oxide Molecular Sensors", Nano Letters, Sep. 2008, 8(10), 3137-40.

Schedin, et al., "Detection of Individual Gas Molecules Adsorbed on Graphene", Nature Materials, 2007, 6(9), 652-655.

Seiyama, et al., "A New Detector for Gaseous Components Using Semiconductive Thin Films", Analytical Chemistry, 1962, 34(11), 1502-1503.

Staii, et al., "DNA-Decorated Carbon Nanotubes for Chemical Sensing", Nano Letters, 2005, 5, 1774-1778.

Zhang, et al., "Improving Gas Sensing Properties of Graphene by Introducing Dopants and Defects: a First-Principles Study", Nanotechnology, Apr. 2009, 20(18), 9 pgs.

\* cited by examiner

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gagtctgtgg aggaggtagt c                                              21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttctgtctt gatgtttgtc aaac                                           24

DNA-DECORATED GRAPHENE CHEMICAL SENSORS

CROSS-REFERENCE TO RELATED APPLICATIONS

This application is a divisional application of now-allowed U.S. patent application Ser. No. 13/637,665, "DNA-Decorated Graphene Chemical Sensors", filed Jan. 10, 2013, which is the National Stage of International Application No. PCT/US2011/030484, "DNA-Decorated Graphene Chemical Sensors," filed Mar. 30, 2011, which claims the benefit of U.S. Provisional Application No. 61/319,062, "DNA-Decorated Graphene Chemical Sensors," filed Mar. 30, 2010. All of the foregoing applications are incorporated herein by reference in their entireties for any and all purposes.

GOVERNMENT RIGHTS

This invention was made with government support under Grant No. DMR-0425780 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Aug. 14, 2015, is named 104377.000186-W5348_SL.txt and is 879 bytes in size.

FIELD OF THE INVENTION

The disclosed invention is in the field of chemical sensing. The field of the invention also pertains to using sensors both individually, in combination, and in array fashion for detecting compounds.

BACKGROUND OF THE INVENTION

The concept of an "electronic nose" has been an active area of research for some decades. Researchers have been trying to provide such a device by attempting to couple an array of chemical odor sensors with a pattern-recognition system. Considerable interest has been generated by the Department of Homeland Security about the use of electronic devices in detecting volatile compounds to prevent explosive, chemical, or biological attacks.

Previous attempts at making electronic noses generally follow the same principle, coupling an array of chemical detectors with pattern recognition systems. However, they differ with respect to the selection of sensors. Common sensor designs include mass transducing, such as quartz microbalance, surface acoustic wave transducers, chemoresistors, and hybrids of such. In any event, it is greatly desired that sensors used for electronic noses and molecular detection exist and function on a very compact— even molecular—scale and exhibit very good electronic properties.

Nose-like sensing schemes derive their organizational principle from biological olfactory systems, where a large number (100s) of sensor types are deployed with broad and overlapping sensitivities to an even larger number of volatile analytes. Reduced graphene oxide, or "chemically derived graphene", has also shown potential as a vapor sensor material where residual oxygen defects (e.g. carboxylic acids or epoxides) provide binding sites for analyte molecules.

Graphene is a single-atom thick, two-dimensional material that has attracted attention because of its unique electronic, mechanical, and thermal properties. Because of these characteristics, graphene is useful in a range of electronic devices—such as sensors—and there is a corresponding interest in methods of producing graphenic materials.

Graphene has been actively studied as a chemical sensor since shortly after it was isolated in 2004. Increasingly sophisticated device processing has revealed that early measurements of graphene chemical sensing responses were amplified by unintentional functionalization.

Graphene is a true two dimensional material with exceptional electronic properties and enormous potential for practical applications. Graphene's promise as a chemical sensor material has been noted, but there has been relatively little work on practical chemical sensing using graphene, and in particular, how chemical functionalization may be used to sensitize graphene to chemical vapors.

Thus, there is a need for improving the ability of graphene to work as a chemical sensor. The invention is directed to these and other important needs.

SUMMARY OF THE INVENTION

The present invention provides a molecular sensor device, comprising: an insulator thin-film disposed directly adjacent to a back-gate substrate; at least one positive electrode disposed directly adjacent to said insulator thin-film, opposite to said back-gate substrate; at least one negative electrode disposed directly adjacent to said insulator thin-film, opposite to said back-gate substrate; and clean graphene disposed between, and in electrical communication with, said positive and negative electrodes, wherein the clean graphene is functionalized with a nucleic acid.

The present invention provides a method of detecting a compound, comprising: contacting a single-stranded DNA functionalized clean graphene sensor device with a medium; monitoring conductance of said single-stranded DNA functionalized clean graphene to determine the presence, absence, or concentration of molecules, or any combination thereof; and correlating a change in conductance to the presence, absence, or concentration of molecules, or any combination thereof.

The present invention also provides a system comprising a plurality of molecular sensor devices comprising: an insulator thin-film disposed directly adjacent to a back-gate substrate; at least one positive electrode disposed directly adjacent to said insulator thin-film, opposite to said back-gate substrate; at least one negative electrode disposed directly adjacent to said insulator thin-film, opposite to said back-gate substrate; and clean graphene disposed between, and in electrical communication with, said positive and negative electrodes, wherein the clean graphene is functionalized with a nucleic acid.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention. However, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figures 1A, 1B:
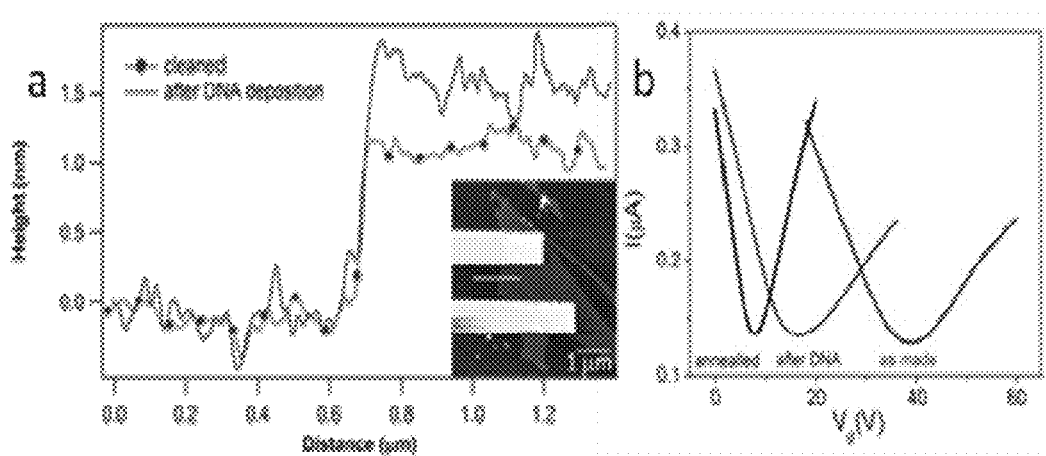
FIG. 1a demonstrates AFM line scans of ssDNA on graphene.
FIG. 1b demonstrates I-$V_G$ characteristics for a graphene device.

The present invention may be understood more readily by reference to the following detailed description, taken in connection with the accompanying figures and examples, which form a part of this disclosure. It is to be understood that this invention is not limited to the specific devices, methods, applications, conditions, or parameters described and/or shown herein, and that the terminology used herein is for the purpose of describing particular embodiments by way of example only and is not intended to be limiting of the claimed invention. Also, as used in the specification, including the appended claims, the singular forms "a", "an", and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about", it will be understood that the particular value forms another embodiment. All ranges are inclusive and combinable.

It is to be appreciated that certain features of the invention which are, for clarity, described herein in the context of a single embodiment, may also be provided separately or in any sub-combination. Further, reference to values stated in ranges include each and every value within that range.

TERMS

"Functionalization", as the term is used herein, is defined as allowing a desired molecular species to be preferentially and specifically bound to the ssDNA. Functionalization thus enhances the sensitivity of the ssDNA-graphene detector as well as the potential range of molecules that can be detected by the ssDNA-graphene sensor.

"Volatile compounds", as used herein, may be considered as compounds vaporized in the atmosphere. The present methods and devices also detect an odor analyte which is considered a sample of the atmosphere to be tested or analyzed.

"Sensor array", as the term is used herein, is defined as a plurality of sensors in accordance with the sensors described herein. The arrays may have different sensors or sets of sensors that are sensitive to a different molecule, molecular family, or genus. The arrays also comprise a data processing system. The system may also comprise a pattern recognition system or other control system.

As used herein, the term "system" is defined as pluralities of field-effect devices, or sensors, and are employed to discriminate among different target molecules.

The chemical sensors described herein function as high sensitivity gas sensors that exhibit conductivity changes in response to odor application. The responses differ in sign and magnitude for different odors, and the odor response characteristics may depend on the physical characteristics of the biopolymer used, such as the base sequence of a ssDNA polynucleotide.

The chemical sensors described presently can be used as the sensor elements in an array of sensors, each with an individualized response characteristic, coupled to an advanced pattern recognition data processing system. Biopolymers provide an extensive library of compounds for the present sensors. Thus, the chemical sensors of the present invention may be produced with sensitivity to a large variety of compounds.

The process begins with chemically clean graphene transistors that are inert to a variety of chemical vapors. The graphene is then purposefully functionalized to generate devices with different chemical sensing responses. Graphene is combined with ssDNA to create a chemically diverse family of vapor sensors for use in a "nose-like" vapor sensing system.

The ssDNA in the DNA-graphene sensor system is not used for its biological functionality, but instead provides sequence-dependent chemical recognition capability, thereby enabling the required number of chemically distinct sensor responses.

Embodiments of the present invention also include methods of using a chemical sensor comprising a substrate that may be semiconducting in some embodiments; an insulating layer; source and drain electrodes on the insulating layer; and, in contact with each of the source and drain electrodes, at least one nanotube having biopolymer thereupon; said method comprising contacting said sensor with an atmosphere sample and detecting the presence or absence of a volatile compound.

A single sample of a sensor may comprise an individual field effect device or may comprise dozens or hundreds of identical field effect devices, being understood that redundancy gives rise to improved accuracy. In any event, a plurality of different sensors is arrayed in a single apparatus with an appropriate controller in electrical communication therewith. Contacting the array with an analyte causes differential responses in the different sensors with the respective currents being evaluated by the controller. The controller is in communication with the computational, evaluative, or other display means in order to reflect the interactions of the sensors with the analyte. Through comparison of the results of the analysis either with prior analysis or with expected values, knowledge of the nature of the analyte may be had.

The molecular sensor device herein has an insulator thin-film thickness of from about 10 nm to about 1000 nm, which covers an area of from about 400 $nm^2$ to covering the entire substrate. The insulator thin-film may be comprised of silicon dioxide, silicon oxide, hafnium oxide, aluminum oxide, titanium dioxide, titanium oxide, or insulating polymer.

The back-gate substrate of the molecular sensor device has a thickness of from about 0.1 mm to about 1 mm, and covers an area of from about 10 $mm^2$ to about 1000 $mm^2$. The back-gate substrate may be comprised of silicon, doped silicon, gallium arsenide, gold, aluminum, or conducting polymer.

The substrate of the molecular sensor device is p-doped or n-doped with 300 nm thermal oxide. The electrodes may be comprised of aluminum, chrome, gold palladium, platinum, titanium, titanium nitride, copper, graphene, or conducting polymer.

The distance between electrodes is from about 10 nm to about 10 µm. the clean graphene covers from at least a portion of the device to covering the entire substrate, which translates to an area of at least 400 $nm^2$.

The hole mobility may be from 500 $cm^2$/V-s to 200,000 $cm^2$/V-s, preferably from 500 $cm^2$/V-s to 5000 $cm^2$/V-s, more preferably from 1600 $cm^2$/V-s to 5000 $cm^2$/V-s, with a doped charge carrier density from about 0 to about $1\times10^{15}$/$cm^2$ at zero gate voltage.

The method of producing the molecular sensing device herein includes monitoring conductance when applying a 1 mV bias and holding the gate voltage at 0. The conductance of the ssDNA functionalized clean graphene is monitored via electrodes that are comprised of gold and chromium.

In view of the foregoing, it is apparent that different individual sensors and assemblages or arrays of either the same or different sensors can be for predefined purposes. Thus, expected responses of sensors in accordance with this invention may be compared with responses from test gasses, liquids, tissues, head spaces, environment samples, and other test samples to determine their contents—either qualitatively or with identical determination of contents. Quantification may also ensue.

Example 1

Graphene transistors were constructed using exfoliated kish graphite. Devices were carefully cleaned to prevent spurious sensing results. Two ssDNA sequences ("Sequence 1" and "Sequence 2") were selected because of their prior use in vapor sensors based on electronic and optical fluorescence readout strategies. The sequences are as follows:

```
SEQ ID NO: 1:
5' GAG TCT GTG GAG GAG GTA GTC 3'

SEQ ID NO: 2:
5' CTT CTG TCT TGA TGT TTG TCA AAC 3'
```

FIG. 1a and FIG. 1b depict AFM line scans of ssDNA on graphene. The inset in FIG. 1a depicts an AFM image with a z-scale of 601 nm. AFM measurements showed that the self-assembled ssDNA layer had a thickness of approximately 0.5 nm, as in FIG. 1a. Although ssDNA films on graphene did not have visible holes or aggregates, AFM revealed an RMS roughness of 0.4 nm, about twice as large as that of pristine graphene.

FIG. 1b shows how the current gate voltage (I-$V_G$) characteristic of an individual electron mobilities were 1000 cm-2/V-s and 750 cm-2/V-s, respectively. The doped charge carrier density (carrier density at $V_G$=0) was $3.3\times10^{12}$/$cm^2$ holes. After the cleaning process, both the hole and electron mobility increased to 2600 $cm^2$/V-s, and the doped carrier density decreased to $6.2\times10^{11}$/$cm^2$ holes. After functionalization with ssDNA, the hole and electron mobilities decreased to 1600 $cm^2$/V-s and 750 $cm^2$/V-s, respectively, indicating slightly increased carrier scattering due to ssDNA on the graphene surface. The final doped charge carrier density was $1.4\times10^{12}$/$cm^2$.

Application of ssDNA led to a shift in the I-$V_G$ minimum, indicating an increase in hole density (FIG. 1b). The polarity of this shift is consistent with chemical gating by negatively charged molecules in the vicinity of the graphene. Using computer models of ssDNA on carbon nanotubes, the adsorption density is approximately $1.5\times10^{14}$ bases/$cm^2$ at 100% coverage.

Example 2

Chemical sensing experiments were performed in a controlled environmental chamber. The device current was monitored while applying a 1 mV bias voltage and zero gate voltage. Initially, Ar carrier gas was flowed through the chamber at a rate of 1 sLm. Analyte gases were substituted for a small percentage of the Ar glow with the total flow rate held constant. For the purpose of comparing changes in response, data are presented as changes in current normalized to the device current measured in a pure Ar flow.

Figures 2A, 2B:
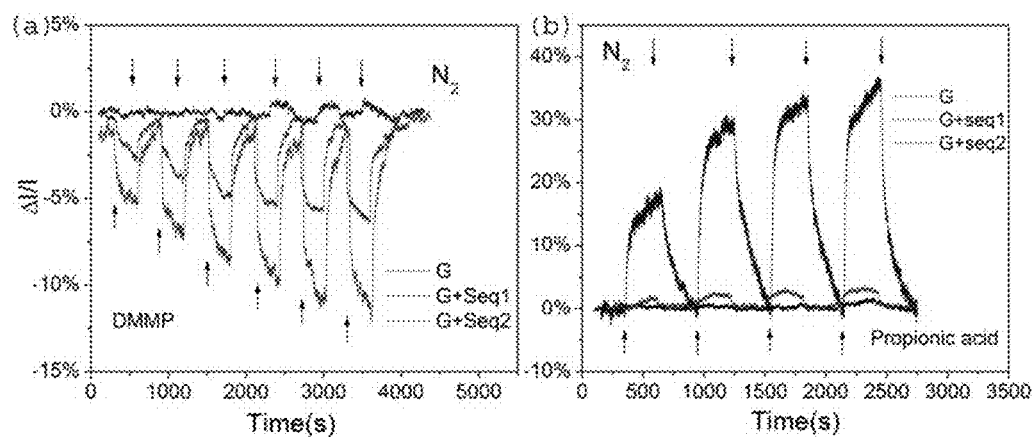
FIG. 2a demonstrates the normalized changes in current versus time for ssDNA-graphene vapor response, with measurements of DMMP at various concentrations.
FIG. 2b demonstrates the normalized changes in current versus time for ssDNA-graphene vapor response with measurements of propionic acid at various concentrations.

FIG. 2a and FIG. 2b depict normalized changes in current versus time for ssDNA-graphene vapor responses, with a comparison of responses to vapors of devices based on clean graphene, and graphene functionalized with SEQ ID NO: 2. The vapors used in FIGS. 2a-2b were dimethylmethylphosphonate (DMMP), a sarin stimulant, and propionic acid, respectively. For both analytes, the current response of clean graphene was very low and barely detectable above system noise, although a response $\Delta I/I_0 \sim 1\%$ was observed at the highest concentrations tested. After coating with ssDNA, enhanced responses on the scale of 5-50% was observed. The sign of the current responses was consistent with a chemical gating effect on the graphene channel where hole conduction dominates.

For both analytes in FIGS. 2a-2b, sensing response and recovery to baseline typically show two distinct timescales. The initial response occurred with a fraction of a second, while the slower equilibrium took several hundred seconds. The lower arrows indicate introduction of analyte at progressively larger concentrations, while upper arrows indicate flushing with pure carrier gas. Clean graphene devices (black data) show very weak vapor responses that are barely above the noise floor. Devices functionalized with SEQ ID NO: 1 data or SEQ ID NO: 2 show significant responses that are sequence-dependent. FIG. 2a embodies measurements of DMMP at concentrations of 20, 40, 60, 80, 100, and 120 ppm. FIG. 2b embodies measurements of propionic acid at concentrations of 90, 220, 435, and 650 ppm.

Example 3

Six different analyte responses are shown in Table 1. Three compounds are homologous aldehydes, with linear chemical formulas $CH_3(CH_2)_N CHO$, where N=5, 6, or 7. The significantly different current responses seen for this sequence shows a chemical differentiation in an atmospheric sensor not often seen outside of biological systems. Molecular dynamics simulations of ssDNA adsorbed onto carbon nanotubes suggests complex conformational motifs may influence the chemical affinity of the device. Similar effects may occur for ssDNA-graphene, leading to a sensing response that is the result of a combination of analyte-DNA and analyte-graphene interactions. Clean graphene devices exhibit very small responses to all analytes at all concentrations tested, with the exception of decanal.

TABLE 1

Sensing Response (ΔI/I0) for Several Analytes

| odor | conc (ppm) | pristine graphene | graphene + seq 1 | graphene + seq 2 |
|---|---|---|---|---|
| DMMP | 20 | <0.1% | −2.5% | −5% |
| Prop Acid | 90 | <0.1% | 1.5% | 18% |
| Methanol | 7500 | 0.5% | 1% | 2% |
| Octanal | 14 | 0.5% | 1% | 3% |
| Nonanal | 0.6 | 0.5% | 2% | 8% |
| Decanal | 1.7 | 4% | 2% | 4% |

When ranges are used herein for physical properties, such as molecular weight, or chemical properties, such as chemical formulae, all combinations, and sub-combinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

---

---

What is claimed:

1. A method, comprising:
   with a nucleic acid functionalized clean graphene sensor device that comprises (i) an insulator thin-film disposed directly adjacent to a back-gate substrate, (ii) at least one positive electrode disposed directly adjacent to said insulator thin-film, opposite to said back-gate substrate, (iii) at least one negative electrode disposed directly adjacent to said insulator thin-film, opposite to said back-gate substrate, and (iv) the clean graphene being disposed between, and in electrical communication with, said positive and negative electrodes and the clean graphene being single-atom thick graphene,
   contacting the nucleic acid functionalized clean graphene sensor device with a medium;
   monitoring a conductance of the nucleic acid functionalized clean graphene; and
   correlating a change in the conductance to the presence, absence, or concentration of molecules, or any combination thereof.

2. The method of claim 1, wherein said contacting is accomplished by flowing the medium over said sensor device.

3. The method of claim 1, wherein the medium is a solid, liquid, gas, or combination thereof.

4. The method of claim 3, wherein the medium comprises analytes.

5. The method of claim 1, whereby monitoring the conductance occurs when applying a 1 mV bias and holding the gate voltage at 0.

6. The method of claim 1, whereby the conductance of the nucleic acid functionalized clean graphene is monitored via electrodes, wherein the electrodes comprise gold and chromium.

7. The method of claim 1, further comprising:
   contacting a plurality of the nucleic acid functionalized clean graphene sensor devices with the medium, wherein each of the sensor devices is functionalized with a different nucleic acid;
   monitoring the conductance of each sensor device; and
   correlating a change in conductance into each device to the presence, absence, or concentration of molecules, or any combination thereof.

8. The method of claim 7, further comprising using a data processing system to send a control signal and receive a data input signal from at least one of the sensor devices, and using a pattern recognition data processing system to detect the presence, absence, or concentration of several molecular species.

9. The method of claim 1, wherein the nucleic acid comprises single-stranded DNA.

10. The method of claim 1, wherein the device has a hole mobility of 500 cm$^2$/V·s to 200,000 cm$^2$/V·s.

11. The method of claim 1, wherein the device has a hole mobility of 500 $cm^2/V \cdot s$ to 5000 $cm^2/V \cdot s$.

12. The method of claim 1, wherein the device has a hole mobility of 1600 $cm^2/V \cdot s$ to 5000 $cm^2/V \cdot s$.

13. The method of claim 1, wherein the device has a doped charge carrier density of about 0 to about $1 \times 10^{15}/cm^2$ at zero gate voltage.

14. The method of claim 1, wherein the medium comprises a gas, a liquid, a tissue, a head space, or an environmental sample.

15. The method of claim 9, wherein the single-stranded DNA is according to SEQ ID NO. 1.

16. The method of claim 9, wherein the single-stranded DNA is according to SEQ ID NO. 2.

* * * * *

UNITED STATES PATENT AND TRADEMARK OFFICE
CERTIFICATE OF CORRECTION

| | | |
|---|---|---|
| PATENT NO. | : 10,168,297 B2 | Page 1 of 1 |
| APPLICATION NO. | : 14/827691 | |
| DATED | : January 1, 2019 | |
| INVENTOR(S) | : Johnson, Jr. et al. | |

It is certified that error appears in the above-identified patent and that said Letters Patent is hereby corrected as shown below:

On the Title Page

Column 2, References cited under OTHER PUBLICATIONS: Replace "Ao, et al., "Enhancement of CO Detection in Al Doped Grapheme", Chemical Physics Letters 2008, 461(4-6), 276-279." with -- Ao, et al., "Enhancement Of CO Detection In Al Doped Graphene", Chemical Physics Letters 2008, 461(4-6), 276-279. --.

Page 2 Column 1, Line 7, References cited under OTHER PUBLICATIONS: Replace "Ishigami, et al., "Atomic Structure of Graphene on Si02", Nano Letters, epub May 11, 2007, 7, 1643-1648." with -- Ishigami, et al., "Atomic Structure of Graphene on SiO2", Nano Letters, epub May 11, 2007, 7, 1643-1648. --.

Column 1, Line 15, References cited under OTHER PUBLICATIONS: Replace "Mohanty, et al "Graphene-Based Single-Bacterium Resolution Biodevice and DNA Transistor: Interfacting Graphene Derivatives with Nanoscale and Microscale Biocomponents", Nano Letters 2008, 8, 4469-4476." with -- Mohanty, et al "Graphene-Based Single-Bacterium Resolution Biodevice and DNA Transistor: Interfacing Graphene Derivatives with Nanoscale and Microscale Biocomponents", Nano Letters 2008, 8, 4469-4476. --.

Page 2 Column 2, Line 1, References cited under OTHER PUBLICATIONS: Replace "Mohanty, et al, On Lie Supporting Document: "Graphene Based Single-Bacteriumm Biodevice and DNA Transistor: Interfacing graphene Derivatives with Nano and Micro Scale Biocomponents", Nano Letters, 2008, 8, 1-18." with -- Mohanty, et al, On Lie Supporting Document: "Graphene Based Single-Bacterium Biodevice and DNA Transistor: Interfacing graphene Derivatives with Nano and Micro Scale Biocomponents", Nano Letters, 2008, 8, 1-18. --.

Column 2, Line 8, References cited under OTHER PUBLICATIONS: Replace "Radosavljevic, et al "Novolatile Molecular Memory Elements Based on Ambipolar Nanotube Field Effect Transistors", Nano Letters, 2002, 761-764." with -- Radosavljevic, et al "Nonvolatile Molecular Memory Elements Based on Ambipolar Nanotube Field Effect Transistors", Nano Letters, 2002, 761-764. --.

Signed and Sealed this
Twentieth Day of August, 2019

Andrei Iancu
*Director of the United States Patent and Trademark Office*